United States Patent [19]

Matsumoto

[11] Patent Number: 5,364,956

[45] Date of Patent: Nov. 15, 1994

[54] DIESTER, COMPOSITE ESTER AND POLYESTER HAVING ETHER-ESTER TERMINAL STRUCTURE

[76] Inventor: Satoshi Matsumoto, 609, 2-3-1, Komeya-machi, Kumamoto-shi, Kumamoto, 860, Japan

[21] Appl. No.: 978,394

[22] Filed: Nov. 18, 1992

[30] Foreign Application Priority Data

Dec. 5, 1991 [JP] Japan .................. 3-348413

[51] Int. Cl.$^5$ .................. C07C 69/76; C07C 69/34
[52] U.S. Cl. .................. 560/89; 560/90; 560/91; 560/94; 560/193; 560/198; 560/199; 252/56 R; 252/56 S
[58] Field of Search .................. 560/89, 90, 91, 94, 560/193, 198, 199; 252/56 R, 56 S

[56] References Cited

U.S. PATENT DOCUMENTS

| | | | |
|---|---|---|---|
| 2,720,502 | 10/1955 | Caldwell | 560/90 X |
| 2,727,881 | 12/1955 | Caldwell et al. | 560/90 X |
| 2,937,996 | 5/1960 | Pethrick et al. | 560/90 X |
| 2,956,954 | 10/1960 | Hoare et al. | 560/90 X |
| 3,336,360 | 8/1967 | Dill et al. | 560/90 |
| 3,336,361 | 8/1967 | Dill et al. | 560/90 |
| 4,661,622 | 4/1987 | Matsumoto | 560/199 |

*Primary Examiner*—Jose' G. Dees
*Assistant Examiner*—Dwayne C. Jones
*Attorney, Agent, or Firm*—Fred Philpitt

[57] ABSTRACT

The compound described in the present invention is represented by the following general formula: $R_1(OCH_2CH_2)_nO(COACOOXO)_m$-$COACO(OCH_2CH_2)_kOR_2$ wherein A is $C_2$-$C_4$ alkylene group or a residual group of aromatic dicarboxylic acid, namely a group formed by removing two carboxylic groups from an aromatic dicarboxylic acid, X is straight or branched chain alkylene group, a residual group of glycols (namely a group formed by removing two hydroxyl groups from a glycol) selected from the group consisting of diethylene glycol, triethylene glycol, dipropylene glycol, and tripropylene glycol, or a residual group of thiodiethanol, n is 1 to 3, $R_1$ is selected from the group consisting of $C_1$-$C_{10}$ alkyl or benzyl, $R_2$ is $C_1$-$C_8$ alkyl or benzyl, m is 0 to 13 and k is 0 to 3.

16 Claims, No Drawings

DIESTER, COMPOSITE ESTER AND POLYESTER HAVING ETHER-ESTER TERMINAL STRUCTURE

BACKGROUND OF THE INVENTION

FIELD OF THE INVENTION

The present invention relates to a process for preparing a plasticizer or a lubricating oil which is primarily used for polyvinyl chloride and which has a high molecular weight and low volatility and has a terminal ether-ester structure(s).

In expressing various compounds in the specification, abbreviated symbols bracketed with "[]" indicate acids, alcohols or groups having a specific meaning defined below. When such a symbol is described alone, it represents a meaning of the symbol in which a terminal hydroxyl and/or carboxyl group is included. When a number of such a symbol or symbols are arranged to indicate bonded state, they represent a meaning of the symbols in which ester or ether linkages are included. For example, the formula $$C_4H_9(OCH_2CH_2)_2OCOACOOX-OCOACO(CH_2CH_2)_2OC_4H_9$$

wherein A is a residual group of adipic acid and X is a residual group of diethylene glycol, it is represented by [BEEAX$_D$AEEB], and the above formula wherein A is a residual group of phthalic acid and X is a residual group of 1,3-butane diol is represented by [BEEPX$_{13}$BPEEB].

| Definition of abbreviation symbols in [ ] | |
|---|---|
| dibasic acid | |
| adipic | A |
| phthalic | P |
| diol component | |
| 1,3-butane diol | X$_{13B}$ |
| 1,2-propane diol | X$_{12P}$ |
| diethylene glycol | X$_D$ |
| terminal etheralcohol component | |
| ethyleneoxy | E |
| diethyleneoxy | DE |
| triethyleneoxy | EDE |
| terminal alkyl | R |
| butyl | B |
| hexyl | H |
| octyl | O |
| methyl | Me |
| benzyl | Bz |

SUMMARY OF THE INVENTION

The compound described in the present invention is represented by the following general formula.

$$R_1(OCH_2CH_2)_nO(COACOOXO)_m-COACO(OCH_2CH_2)_kOR_2$$

wherein

A is $C_2$–$C_4$ alkylene group or a residual group of aromatic dicarboxylic acid, namely a group formed by removing two carboxylic groups from an aromatic dicarboxylic acid X is straight or branched chain alkylene group, a residual group of glycols (namely a group formed by removing two hydroxyl groups from a glycol) selected from the group consisting of diethylene glycol, triethylene glycol, dipropylene glycol, and tripropylene glycol, or a residual group of thiodiethanol, n is 1 to 3, $R_1$ is selected from the group consisting of $C_1$–$C_{10}$ alkyl or benzyl, $R_2$ is $C_1$–$C_8$ alkyl or benzyl, m is 0 to 13 and k is 0 to 3.

More particularly, the present invention relates to a process for preparing a compound having a structure of the following formula A or B depending on the type of the used dicarboxylic acid. Formula A is further classified into A-1 to A-3.

$$RO(CH_2CH_2O)_nO(COACOOXO)_mCO(CH_2)_4COO(OCH_2CH_2)_nOR \quad (A)$$

$$RO(CH_2CH_2O)_nO(CO(CH_2)_4COOXO)_mCO(CH_2)_4COO(OCH_2CH_2)_nOR \quad (A-1 \text{ and } A-2)$$

(A-1: [REE(AX)$_m$AEER] or A-2: [REE(AX)$_m$AR] m = 1–20)

$$RO(CH_2CH_2O)_nOCOC_6H_4COOX(OCO(CH_2)_4COOXO)_mCOACOO(OCH_2CH_2)_{0-3}OR$$

(A-3: n = 1–3, [REEPX(AX)$_m$PEER] or [REEPX(AX)$_m$AR], m = 1–20), $$R(OCH_2CH_2)_{1-3}OCO C_6H_4COOR (B: [REEPR'])$$

wherein R and R' outside the bracket "[]" indicate alkyl groups.

DESCRIPTION OF PRIOR ART

Composite esters having a structure of RO(COACOOXO)$_m$COACOOR have been reported as an useful lubricating oil as first reported by Smith. I have also reported methods of their preparation and their properties, and have reported their usefulness as a plasticizer for polyvinyl chloride ("Kobunshi Ronbunshu" (Reports on High Polymers), vol147, No.3, 177). Also, I have reported compounds having a terminal ether-ester group in 41th Meeting for the Discussion on Polyvinyl Chloride (December,1990) and filed a patent application in Japan (Japanese Patent Application Hei3-157460).

Process for preparing diesters of phthalic acid and diesters of adipic acid are known. They are mainly produced by a dehydration esterification reaction. The catalysts used in the reactions were sulfuric acid and para-toluene sulfonic acid in the old days. In recent years alkoxy titaniums are used.

DETAILED DESCRIPTION OF THE INVENTION

The present invention relates to esters having a terminal ether-ester structure produced in accordance with a dehydrating esterification reaction. In the conventional production processes for polyesters and composite esters, alkyl esters (or alcohol) have been used for terminal groups. The resulting esters are always a mixture of esters having a broad molecular weight distribution with different values of m in the above-mentioned general formula and a molecular weight different from the desired molecular weight. For example, when a compound wherein m=1 is to be selectively synthesized, the product with increased proportion of the compound of m=1 is obtained only in a condition where a great amount of by product diesters is produced. Thus, a large excess amount of the dibasic acid must be reacted with the diol.

On the other hand, a process for controlling the molecular weight distribution by the use of a monobasic acid is reported in the production of a polyester. Oligomers are also produced as by-products in this process. Removal of the oligomers are difficult to attain. Thus, this process cannot be used for the production of the polyester without problem. It has been studied to produce polyesters such as those where m=1 which do not contain oligomers.

Although not 100% sufficient in terms of the results of the molecular weight distribution, the present invention relates to a process for producing the titled high molecular weight esters in which by-product low volatile materials are extremely reduced.

In the process of producing the polyesters of the present invention, by-product volatile materials produced are below 10% even when m is 1, and as the molecular weight increases, the volatile material by-products are scarcely produced. The present invention relates to such a process for preparing the esters, and plasticizers using the esters. When usual alkyl esters with m=1 is tried to be produced, it is known that oligomer mixtures up to m=7 is produced in a reaction of stoichiometric quantities. The mode of reaction is described as

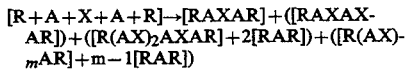

wherein R is monohydric alcohol, A is dibasic acid and X is diol. Namely, oligomers having m of 2 to 7 is always produced as by product with the distribution shown by $(AX)_m$. The diester by-product shown as $m-1[RAR]$ is produced. There are problems of not only the absence of selectively to [RAXAR], but also the abundance of the recovered amount of [RAR]. Thus, too much by-products are produced in the process. Although the by-product [RAR] is eliminated if the molecular weight can be controlled and 100% [RAXAR] can be produced, only less than 50% [RAXAR] can be produced in the reaction at stoichiometric amounts. Thus, the point is how the amount of by-product [RAR] (hereinafter referred to as diester) is reduced.

On the other hand, I have reported transesterification processes for the production of compounds having ether-ester structure. The transesterification processes are employed for the production of high molecular weight esters because reactions proceed slowly and there is a drawback of coloring in dehydration esterification processes. However, when esters having terminal ether-ester structure are produced in relation to the study of this technology, it has been found that even dehydrating esterification processes allow one to obtain a very characteristic esterification product which has a narrow width of molecular weight distribution, and hence the process is advantageous for producing esters with small by-products.

DETAILED DESCRIPTION OF THE INVENTION

In the production of these objective esters, the present technology is characterized by the use of polyethylene glycol monoalkylether as the terminal alcohol(s). The greatest advantage is that production of by-product low molecular weight oligomers is extremely small compared with conventional processes and that products with low viscosity can be obtained. Particularly, the notable point in the production technology is not to use excess amount of alkylalcohol but to proceed the reaction with approximately the equivalent amount of alcohol and to carry out the esterification reaction by adding necessary amount of an alcohol equivalent to the acid value measured. It is necessary to obtain the product thus avoiding widening of the molecular weight distribution of the product. When it is sufficiently controlled, as also shown in examples, production of by-products is extremely small even with m=1, thus resulting in esters mainly of a desired molecular weight. The low molecular weight composite esters thus produced are of low viscosities, and when they are used as a plasticizer of polyvinyl chloride, they provide excellent plasticizing efficiency.

The composite esters have the structure of the previously shown general formula and they are prepared from dibasic acid, diol, and monohydric alcohol. Since polyethylene glycol monoalkylether is a monohydric alcohol, the resulting esters produced by using it is naturally a compound as imagined. But generally, an excess amount of an alcohol is used for the production of the esters. Thus, by the surplus amount of the alcohol, polyesters once produced undergo transesterification. As a result, molecular weight distribution is widened and low molecular weight oligomers are produced as by-products. A series of studies of composite esters have revealed this fact. Thus, it has been found that an excellent process for the production is attained when the use of polyethylene glycol monoalkylether is combined with technology in which molecular weight distribution is take into account. Thus, use of polyethylene glycol monoalkylether as a monohydric alcohol alone cannot attain the desired purpose sufficiently. But this etheralcohol forms a coordinating complex with titanium, a catalyst for esterification. As a result, it is considered that once produced esters do not easily undergo transesterification, and that the etheralcohol acts advantageously as a terminal alcohol to control the molecular weight distribution. Consequently, the catalyst used is preferably a titanium catalyst. In particular, since polytitanic acid catalyst provides a reaction mechanism of primary esterification reaction to an acid, the acid value is sufficiently reduced with time even with the addition of an alcohol in amounts equivalent to the acid value in proportion to the logarithm of the amount of the remaining acid. As a result, dehydration esterification reaction can be sufficiently carried out and the molecular weight distribution can be controlled. As an example to show a product with narrow MW distribution is not necessarily produced when the terminal group is of polyethylene glycol monoalkylether, a butyl terminal composite ester with m=1 which was distilled and purified is subjected to trans-esterification with an excess amount of the ether-alcohol to produce a titled compound having ether-ester terminal structure. In this case, the diester is formed in great quantities and the MW distribution has been widened. The viscosity of the product is high. Thus, it is understood that the product must be prepared in a condition where trans-esterification reaction does not occur. Concretely, the condition is to reduce the excess amount of the monohydric alcohol as much as possible, and to carry out the dehydration esterification reaction by supplementing an alcohol in amounts equivalent to the acid value.

The esters thus obtained generally are more viscous in proportion to their molecular weight and have poorer plasticizing efficiency when used as a plasticizer for polyvinyl chloride. The greater the degree of polymerization and the number of m in the general formula, the higher the viscosity of the composite esters and the polyesters. Thus, the smaller the value of m, the better the performance for the purpose of low viscosity and high plasticizing efficiency. Although composite esters having a small molecular weight of $m=1$ or $m=2$ cannot be completely free from oligomer byproducts, it is considered that, according to the process of the present invention, the amount of the by-product is extremely small and hence the viscosity of the product is smaller as compared with the products of conventional processes and hence esters with narrow MW distribution can be produced. Particularly, when diethylene glycol monoalkylether is used in the reaction, it easily forms a complex salt with the catalyst. The rate of its esterification reaction is slower than conventional alkylalcohols. But it contributes to control the molecular weight by staying in the molecule selectively as a terminal group or terminal groups for a reason that either it reacts selectively as terminal group due to slower reaction rate compared with the diol, or the produced ether-ester linkage is relatively resistant to changes by trans-esterification.

The ether compound used as the terminal alcohol is a monoalkylether such as methyl-, ethyl-, butyl-, hexyl-, octyl- or benzyl-ether. The ethylene glycols are mono-, di- and triethylene glycols. Preferably, diethylene glycol monoalkylether is used.

The amount of the ether-alcohol used in the reaction is the necessary amount as the terminal component(s). Thus, one or two moles are added in the reaction of the dibasic acid component and the diol component corresponding to the molecular weight. Among the ways of addition to the reaction system, the best results are obtained if the addition is at the stage when the dehydration esterification has advanced and oligomers are about to be formed. However, even when the ether alcohol is partially added to the reaction system, diester formation is relatively small and exhibited tendency is completely different from a reaction in which a conventional alkylalcohol is used. This is an excellent feature of this reaction system. Since acid value does not decrease sufficiently when the terminal alcohol component is consumed in forming a diester, it is necessary to complete the esterification reaction by adding a small amount, equivalent to the acid value, of a monohydric alcohol or a diol at the end. Since the addition of an alkylalcohol is a cause to broaden MW distribution, the smallest possible amount is preferably added. Concretely, it is prepared that an amount of an alcohol equivalent to the amount of the remaining acid is added when the acid value is as low as from ten several milligrams to several milligrams and allow the reaction to proceed.

As the terminal alcohol component, 2 moles of the ether-alcohol is used. Alternatively, a half the amount may be added as the ether-alcohol at the early stage of the reaction and the remaining amount may be added as an alkyl alcohol to the reaction system to make esters having different terminal groups (A-2). In this case, it is thought that distribution is somewhat broadened and volatile materials are increased depending on the used alkyl alcohol. As other monohydric alcohols used as a mixture, octanol and benzyl alcohol may be used in view of compatibility with DOP, a conventional plasticizer, and in an expectation to improve electrical properties. A small amount of a long chain alcohol or other alcohols may be added. The used ratio need not necessary be fifty-fifty (5:5) but it may be 6:4 or 7:3.

When a stoichiometric amount of the terminal alcohol is used, a long period of time is required to render the acid value to a necessary value for the ester, and a low acid value is difficult to attain. Thus, a small amount of a low molecular weight alcohol is added at the end. The resulting product is a polyester mixture with somewhat broad MW distribution and with low molecular weight terminals. The acid value can be reduced. When low molecular weight butanol is used, the smaller the used amount and shorter the reaction time, the better the result because trans-esterification proceeds. Also, it is preferred to carry out transesterification equivalent to the remaining terminal alcohol derived from the excess amount. To attain this, volatile materials are distilled off by heating and agitating at 160° to 220° C. under reduced pressure after the dehydration esterification reaction to adjust the molecular weight.

The catalyst used is a titanium catalyst. In addition to alkoxy titanium such as butyl titanate, polyolpolytitanate prepared from an alkoxy titanium and a diol used for the reaction, hydrolyzed product thereof or activated polytitanic acid solid catalyst are advantageously used. They are recommended to obtain low acid value products because of small coloring, and because reaction rate does not become slow at the late stages of the reaction.

A particularly important factor is the necessity of controlling the reaction amount of the used diol because the diol is distilled in admixture with the distillate water of the dehydration esterification reaction.

The polyesters obtained is higher in viscosity and lower in plasticizing property as the proportion of aromatic groups incorporated into the esters increase, when compared with polyesters in which adipic acid alone is used. Phthalates are less volatile than adipates and show good resistance to chemicals. Migration to polyethylene and to polyvinyl chloride is improved to result in good electric resistance values. From these viewpoints, excellent properties can be expected from heterogeneous composite esters having aromatic group(s) in the molecule. It is possible to produce polyesters of adipic acid having polyethylene glycol monoalkylether structure at one of the terminals by preliminarily reacting phthalic anhydride and polyethylene glycol monoalkylether and using it or using polyethylene glycol monobenzylether. Also, polyesters having aromatic group(s) can be prepared by using at first polyethylene glycol monoalkylether for one terminal of a polyester of adipic acid and using benzyl alcohol for the other terminal.

Trans-esterification reaction can be controlled by reacting polyethylene glycol monoalkyleter and phthalic anhydride and then carrying out dehydration esterification reaction with an alkyl alcohol. Thus, compound (B) having each of the ester structures in the molecule can be obtained in a relatively high yield. Actually, it is not that transesterification does not occur at all in this reaction, but trans-esterification partially proceeds. However, the purity is increased by using a small amount of alkylalcohol. A small amount of trans-esterification reaction products can be tolerated in a plasticizer. Thus, a plasticizer which has better plasticizing properties than commonly used plasticizer of DOP, and which is of small volatility and resistant to coldness is obtained. Even if one tries to obtain a compound of the general formula

R(OCH$_2$CH$_2$)$_{1-3}$OCOACOOR (B:[REEPR]), a mixture of the compounds represented by [REE-PEER] and [RPR] is obtained when trans-esterification proceeds. If trans-esterification is carried out between DOP represented by [RPR] and an equivalent amount of an ether alcohol represented by [REE]OH, approximately equal amounts of two products are produced (see the report of the meeting). Also, when an excess amount of a monoalcohol is used and the dehydrating esterification is carried out, similar mixture of esters are obtained. In contrast, the amount of byproduct DOP is small in the process of the present invention and a compound represented by [REEPR] is mainly obtained. When it is used as a plasticizer, volatility as compared with DOP is smaller generally as the molecular weight increases although volatility depends on the group of R, and the obtained product has a volatility approximately 60 percent of that of DOP, and has an equivalent or better plasticizing property and good low temperature properties.

When the product is used as a plasticizer for polyvinyl chloride, the primary characteristic is extremely lower volatility corresponding to the molecular weight. The amount of migration to polyvinyl chloride resin is smaller in response to the structure, and improvement in resistance to chemicals and some improvement in surface electric resistance are obtained concurrently. Those with a methyl or an ethyl terminal have poor water resistance and electric properties but they have good plasticizing property. In the case of composite esters, extremely good plasticizing property and at the same time excellent low temperature properties are shown. The viscosity is increased as the polyester is formed. But the produced plasticizer has lower viscosity compared with commercial polyesters, and its deterioration in plasticizing property is small, and it has small volatility, and its migration in polyvinyl chloride is small, and its migration into polyethylene and migration by gasoline extraction is small. Since low molecular weight fractions are small, influence by the difference in molecular weight is great. On the other hand, as an influence of the type of the dibasic acid, when an aromatic group is incorporated, A3 group in which the terminal group is benzyl or phthalic acid is used for the terminal group shows increase in viscosity influenced thereby. But the amount of migration is small and property against volatilization and resistance to gasoline are improved. These esters having terminal polyethylene glycol monoalkylether show differences in performance depending on their structure and the diol component. If there is a 1,2-propanediol component, volatility is high. To carry out the reaction in theoretical amounts, recovery of the diol from distillate water is a problem. The product is generally low viscous and highly plasticizing. 1,3-butane diol is most commonly used. Use of diethylene glycol result in rapid esterification and ease of obtaining low acid value products to show a feature in production process. Low temperature properties are improved, polarity of the product is increased, viscosity is somewhat high, and plasticizing property becomes somewhat poor. Also, by rendering the terminal(s) to ethylene glycol monohexyl or monooctyl structure, it is found that fungicidal property is shown.

EXAMPLES

In example 1-17, is explained A-1:[REE(AX)$_m$AEER], and in examples 18-24, A-2:[REE(AX)$_m$AEER], and in examples 25-32, A-3:[REEPX(AX)$_m$PEER] and [REEPX(AX)$_m$AR] and then B:[REEPR]. The combination of alkyl group and diol component are not limited to those disclosed in Examples.

EXAMPLE 1

Di-butoxyethyleneoxyethyl mono(1,3-butanediyl adipate) [BEEAX$_{13B}$AEEB]

To 45 g of 1,3-butanediol, is added 1 g of a catalyst prepared from 1,3-butanediol and tetrabutoxy titanium and subjected to activation treatment. They are stirred and suspended and 146 g (1 mole) of adipic acid is added to start dehydration esterification reaction. Until ¼ amount(10 ml) of water is formed, 162 g (1 mole) of diethylene glycol monobutylether is added dropwise. Water recovered is 36.5 ml as against calculated amount 36 ml. When the acid value is 2, 10 g (0.07 mole) of diethylene glycol monobutylether is supplemented portionwise in response to acid value to continue dehydration esterification reaction. Four hours later, acid value is 0.12 and the reaction is completed. Volatile materials formed are removed under reduced pressure of 20 mmHg at 160° to 200° C., to complete the reaction. The temperature is decreased to 100° C. and 10 ml of water is added. After one hour stirring acid clay is added and they are stirred and filtered to remove catalyst residue. A calculated amount of alkali is added and they are washed with hot water. Volatile materials are removed under reduced pressure, and from distillation under reduced pressure, 13 g of a fraction boiling 185–210/0.4 mmHg is recovered. This fraction is di-dibutyloxyethyleneoxyethyl adipate (DBEEA, hereinafter indicated by this abbreviation). They are collected and subjected for distillation for purification to give a component useful as a plasticizer having a viscosity of 32 cP, plasticizing efficiency 45, softening temperature −48.3° C., electrical surface resistance 6.0×10$^8$, volatility loss 9.01, 2.17, and 17.42. On the other hand, objective BEEAX$_{13B}$AEEB having 138 cP is obtained in the residual liquid. It has a plasticizing efficiency of 48, softening temperature of −32.3° C., volatility loss of 4.0% (value used is 160° C. for 2 hours in hot air circulating heating oven), migration % after 12 hours at 60° C. from 50 phr polyvinyl chloride sheet to 10 phr polyvinyl chloride sheet (hereinafter referred to as migration %) of 6.4% which is greater than 3.0% of DOP. Although it has greater migration %, it is more soluble in polyvinyl chloride. Migration % after 12 hours under the same condition to a polyethylene sheet is 1.8% which is a very small value compared with 6.5% of DOP.

EXAMPLES 2–4

The reaction is carried out by adding diethylene glycol monobutylether [BEE]OH portion wise as soon as the dehydration esterification is started. The esterification reaction is carried out using a small amount of butanol equivalent to the acid value to reduce the acid value and then transesterification reaction is taken place. Thus, the MW distribution is broadened but relatively pure composite esters of m=1 is formed as a mixture with diesters. When the mole ratio of the reaction is varied, the viscosity and plasticizing efficiency of the products are as follows.

| Example | mole ratio* | by-product amount | viscosity of products | plasticizing efficiency |
|---|---|---|---|---|
| 2 | 3:1:4 | 0.93 | 98(48) | 70(47) |
| 3 | 2.5:1:3 | 0.51 | 141(50) | 123(48) |
| 4 | 3:1:3H | 1.25 | 122(48) | 83(47) |

*(adipic acid:diol:diethylene glycol monobutylether)

The by-product amount is moles of produced DBEEA boiling at 165–210/0.5 mmHg and the necessary ratio of the amounts for the composite ester from the reaction of adipic acid:diol:diethylene glycol monobutylether is 2:1:2. From the excess part of the amounts, the by-product diester is formed from the ratio of 1:0:2. From the molar ratio of the reaction of Example 2, one mole of the by-product is to be formed. The actual result is 0.93 mole of the by-product. Theoretically, 0.5 mole of the by-product is to be formed from Example 3 and it is seen that the reaction proceed approximately in quantitative amounts. Example 4 exemplify concurrent use of octanol. Extra amount corresponding to 25% of the diester is formed. The terminal group from octanol is incorporated in the product and MW distribution becomes unfavorable. It is thought that more oligomers where m is 2 or greater are formed. The product viscosity and (plasticizing efficiency) in the second column is showing the case where the diesters are mixed in the ratio as formed. Also, those with terminal ether-ester group are difficult to separate unlike those with alkyl terminal, and MW distribution cannot be determined. When the mole ratio of the reaction is changed so that the mole of the acid is higher, the viscosity of the product is lower. This is a feature of composite esters which is thought to make the MW distribution narrower. Thus produced composite ester can be used as it is as a less volatile plasticizer for low viscosity low temperature use without separating DBEEA by distillation.

| | |
|---|---|
| Example 2 | 70 cp, plasticizing efficiency 47, heat loss 5.9%, softening temperature −31.0° C. |
| Example 3 | 123 cp, plasticizing efficiency 48, heat loss 5.3%, softening temperature −27.9° C. |
| Example 4 | 83 cp, plasticizing efficiency 47, heat loss 6.5%, softening temperature −30.5° C. |

EXAMPLE 5

To 45 g of 1,3-butane diol, is added 1 g of polyol polytitanate catalyst and they are stirred and suspended. Dehydration esterification reaction is stated by adding 146 g (1 mole) of adipic acid and 162 g (1 mole) of diethylene glycol monobutylether. The reaction is continued by recycling the distillate water. As the excess alcohol, butanol is added during dehydration esterification reaction. The used amount of butanol is 45 g. After 4 hours 37.0 g of water is obtained and the reaction is completed at the acid value of 0.19. Trans-esterification is carried out at 180°–200° C./20 mmHg to recover 48.6 g of butanol. In a usual manner, the catalyst is removed and the solvent is removed, and after distillation, 77 g of diester consisting mainly of DBEEA of bp of 150°–210° C./0.5 mmHg, viscosity of 123 cp is produced. The residual liquid of distillation is 220g, 70% and the viscosity is 141 cp. Trans-esterification proceeds during the esterification and butanol substituting reactions. As a result, diesters are produced as a by-product in a large quantity and the product is a highly viscous mixture containing a large quantity of oligomers. In this reaction, DBEEA is formed at an early stage of the reaction. Thus, the product composite ester contains high percentage of oligomers. In this case, the by-product is a mixture with DBEEA which can be used as an excellent plasticizer and described in Example 1 although volatility is somewhat high, and can be used as a plasticizer.

EXAMPLES 6–7

Dibutylethyleneoxyethyl (1,2-propanediyl adipate), dibutylethyleneoxyethyl (ethyleneoxyethanediyl adipate) [BEEAX$_{12P}$AEEB][BEEAX$_D$AEEB]

In the some manner as in Example 1, using 1,2-propane diol ($X_{12P}$) (Example 6) or diethylene glycol ($X_D$) (Example 7) as the diol component, the reaction is carried out, and volatile materials are distilled off at 240° C./0.5 mmHg, and the product of the residual liquid is obtained in the yields of 92.4% and 91%, respectively. Their value of viscosity, plasticizing efficiency, heat loss, electric resistance, and percentages of migration to PVC and migration to PE are shown in Table 1.

EXAMPLE 8

Di-hexylethyleneoxyethyl (1,3-butanediyl adipate) [HEEAX$_{13B}$AEEH]

After reaction is carried out in the same manner as in Example 1 using 2 mole equivalents of diethylene glycol monohexylether, the product is distilled. There is little distillate at 270° C./0.4 mmHg and the product is obtained as a residual liquid from the distillation. The properties of the product are shown in Table 1.

EXAMPLE 9

Di-butoxyethyleneoxyethyl di-(ethyleneoxyethanediyl adipate) [BEE(AX$_D$)$_2$AEEB]

To 2 mole equivalents of diethylene glycol (70.7 g, 0.66 mole), is added 1 g of polyol-polytitanic acid catalyst, and they are heated. To the mixture, is added 3 mole equivalents of adipic acid (146 g, 1 mole) and dehydration esterification reaction is started. Immediately thereafter dropwise addition of 2 mole amount of diethylene glycol monobutylether is started. When the amount of water distillate is half the calculated amount, the dropwise addition is completed. Water is recycled to the reaction liquid, the temperature is reduced, water is distilled off and then reaction is continued. When nearly the calculated amount of water has been removed and the acid value is 2, esterification is caused to proceed while supplementing diethylene glycol in calculated amounts equivalent to the acid value. After 4 hours, the acid value is 0.09. Water is added and they are heated and stirred. The catalyst is precipitated and filtered with acid clay. After washing with an alkali and water, volatile materials are removed by distillation under reduced pressure at 280° C./0.5 mmHg at the highest to yield the product. The amount of produced volatile materials is 15 g. The viscosity of the product [BEE(AX$_D$)$_2$AEEB] is 421 cP. The properties and performances are shown in Table 1.

EXAMPLE 10

Di-Butoxyethyleneoxyethyl tri(1,3-butanediyl adipate) [BEE(AX$_{13B}$)$_3$AEEB]

To 67.5 g (3/4 mole) of 1,3-butane diol and 1 g of polytitanic acid catalyst, is added 146 g (4/4 mole) of adipic acid and dehydration esterification reaction is started. The reaction is caused to proceed with recycling, water to the reaction vessel. When ¼ amount of water is distilled, 81 g (2/4 mole) of diethylene glycol monobutylether is added portionwise. When the acid value is 3, 10 g of etheralcohol is added and the reaction is completed at an acid value of 0.2. Work-up is carried out in a conventional manner as described above, and when 3 ml of volatile materials are removed at 195°-210° C./0.4 mmHg, there is obtained a residual liquid boiling at 270° C./0.4 mmHg in 85% yield. The viscosity is 398 cP, and the plasticizing efficiency is 51. It has a maximum value at m=3 in distribution measurement results according to Shodex GPC KF-804, 803,802 (8×300mm) THF 1 ml/min. As against the theoretical molecular weight of 1034, it has Mn of 891 and Mw of 1134. Other properties are shown collectively in Table 1.

EXAMPLE 11

Di-Butoxyethyleneoxyethyl tri(1,2-propanediyl adipate) [BEE(AX12P)$_3$EEB]

A reaction is carried out in the same manner as above using 58.4 g (¾ mole) of 1,2-propane diol. But the reacted amount is small due to insufficient recycling of 1,2-propane diol. Namely, distilled amount of water is as much as 42 g as against the calculated amount of 36. Thus, since the acid value does not decrease, transesterification by addition of butanol is carried out to obtain the product. Perhaps, the product has a molecular weight lower than desired, and is a mixture of esters having a relatively wide molecular weight distribution. By distillation, 48 g of volatile materials boiling 160°-210° C./0.8 mmHg is produced as by-products. The viscosity is 301 cP and the plasticizing efficiency is 54.

EXAMPLE 12

Diethoxyethyleneoxyethyl tri(1,3-butanediyl adipate) [EEE(AX$_{13B}$)$_3$EEE]

In the same manner as above, the reaction is carried out. There is little forerun, and a product is obtained as a residual liquid of distillation at 290° C./0.6 mmHg in 90% yield, with a viscosity of 431 cP and a plasticizing efficiency of 47.

EXAMPLE 13

Di-hexyloxyethyleneoxyethyl tri(1,3-butanediyl adipate) [HEE(AX$_{13B}$)$_3$EEH]

In the same manner as in Example 11, using the same size of reaction scale, 4% excess 1,3-butane diol and 2/4 mole of diethylene glycol monobutylether are added to the reaction system by the time when ¼ of the reactants has been reacted. The acid value is reduced down to 0.15 by excess amount of the etheralcohol (3.4 g), and the reaction is worked up in the conventional manner and a residual liquid boiling above 280° C./0.7 mmHg is obtained by distillation. The yield is 93.5% and the viscosity is 493 cP and the plasticizing efficiency is 51.

EXAMPLE 14

Benzyloxyethyl tri(1,3-butanediyl adipate) [BzE(AX$_{13B}$)$_3$AEBz]

To 4/4 mole of adipic acid and ¾ mole of 1,3-butane diol, is added 1 g of a solid titanic acid catalyst to start dehydration esterification reaction. When the distilled amount of water is ⅓, 76 g of ethylene glycol monobenzylether is added dropwise. Water is recycled and returned to the reaction liquid when the reaction proceed. To reduce the acid value, a total of 12 g of butanol was added in a manner to correspond to the reduction of the acid value, until the acid value is 0.08. A small amount of volatile materials from transesterification is removed at 180° C./15 mmHg and the reaction is complete. By working-up in conventional manner, 5.6 g of DBzA is removed by distillation. A product 215.8 g is obtained as a residual liquid in 5 85.1% yield with a viscosity of 544 cP.

EXAMPLE 15

Dimethyloxydiethyloxyethyl tri(ethyleneoxyethanediyl adipate)[MeDEE(AXD)3AEDEMe]

To 4/5 mole of adipic acid and 3/5 mole of diethylene glycol, is added 1 g of polytitanic acid catalyst prepared from diethylene glycol and tetrabutoxytitanium to start dehydration esterification reaction. To the mixture, is added 2/5 mole of triethylene glycol monomethylether. The distillate is recycled once to the reaction liquid. The acid value is reduced by adding 1 g of diethylene glycol and 6 g of etheralcohol corresponding to the acid value, and the reaction is complete at an acid value of 0.1. After work-up in a conventional manner, little distillate at 280° C./0.8 mmHg from distillation can be obtained. The product is obtained as a residual liquid. The viscosity is 970 cP.

EXAMPLE 16

Di-butoxyethyleneoxyethyl octa(1,3-butanediyl adipate) (A-1)[BEE(AX$_{13B}$)$_8$AEEB]

To a mixture of 90 g (8/8 mole) of 1,3-butane diol and 1 g of a catalyst, is added 164.3 g (9/8 mole) of adipic acid to start dehydration esterification reaction. The dehydration esterification reaction is carried out by adding diethylene glycol monobutylether (2/8 mole) in portions so that 20 g is added before the half amount of water is distilled and the remaining 20.6 g is added after 20 ml of water is distilled. In the course of the reaction, the temperature is reduced, and distilled water which contains the diol is subjected to distillation for three times, and the unreacted diol is returned to the reaction system and reacted thoroughly. After esterification reaction for 4 hours, and when the acid value is 2.5, 10 ml of butanol is added in two portions. After further two hours, at the time when the acid value is 0.2, the reaction is completed and work-up to remove the catalyst is carried out in a conventional manner followed by distillation. As forerun, 4.5 g of volatile materials are removed to give 228.8 g (90%) of a residual liquid from distillation boiling above 270° C./0.5 mmHg. The viscosity at 21° C. is 1569 cP yand the plasticizing efficiency is 57. The distribution measurement results according to GPC is Mn=1395 and Mw=1901 as against the calculated molecular weight of 2034. It is a polyester having a maximum value for the molecular weight of 1814.

EXAMPLE 17

Di-Butoxyethyleneoxyethyl trideca(1,3-butanediyl adipate) [BEE(AX$_{13B}$)$_{13}$AEEB]

To a mixture of 117 g of 1,3-butane diol (13/10 mole) and 1 g of a catalyst, is added 204.4 g (14/10 mole) of adipic acid to start dehydration esterification reaction. In the course of the reaction 32.4 g (2/10 mole) of diethylene glycol monobutylether is added and dehydration esterification reaction is carried out while recycling water at a low temperature. 54 ml of water is distilled. The esterification reaction is caused to proceed by adding 20 g of butanol at an acid value between 5 and 1, and the reaction is completed at an acid value of 0.2. Work-up in a conventional manner is carried out for this ester mixture and for an ester obtained by removing butanol produced by transesterification at 160°–200° C./15 mmHg, and a product liquid as a residual liquid of distillation boiling above 270° C./0.5 mmHg and having a viscosity of 1006 cP as well as a product liquid for which the trans-esterification is carried out having 1970 cP are obtained. A polyester having Mn of 1198, Mw of 1549 as against theoretical molecular weight of 3034, and a maximum value of the distribution at a molecular weight of 1315, as well as a polyester mixture having Mn of 1352, Mw of 1858 and a maximum value of molecular weight distribution at a molecular weight of 1833 are obtained. Although the molecular weight is decreased by using butanol to form low acid value esters, and the average molecular weight is increased by the transesterificaiton, the width of the distribution is widened by these treatment. Mw/Mn=1.374. The results when these products of Examples 1 to 18 are used as a plasticizer is summarized in Table 1.

EXAMPLES 18, 19, 20

Butylethyleneoxyethyl 2-ethylhexyl mono-, di- or tri- or octa-(1,3-butanediyl adipate)(A-2) [BEEAX$_{13B}$AO], [BEE(AX$_{13B}$)$_3$AO], [BEE(AX$_{13B}$)$_8$AO]

After the reaction of adipic acid (2/2, 4/5 or 9/8 mole), 1,3-butane diol(½, 3/5 or 8/8 mole), and diethylene glycol monobutylether (½, 1/5 or ⅛ mole), dehydration esterification reaction is carried out by adding octanol (½ mole, 65 g, 26 g or 17 g) to the reaction system portionwise at the end. To reduce the acid value, 8 g to 10 g excess amount of ocatanol is added so that an acid value of 0.2 to 0.1 is obtained. In a conventional manner, work-up and distillation is performed. Volatile materials of 170°–220° C./0.5 mmHg are produced in 94 g, 24 g or 11 g amounts, and the products are obtained as a residue in 185 g (62%), 160 g (80%), and 205 g (83%) amounts. By the addition of octanol and esterification, the transesterification proceeds and more by-products are obtained. Their viscosities at 21° C. and plasticizing efficiency are summarized in Table 2. It is assumed that the molecular weight is somewhat lower than desired.

EXAMPLE 21

Butoxyethyleneoxyethyl 2-ethylhexyl di(ethyleneoxyethanediyl adipate) [BEE(AX$_D$)$_2$AO]

According to Example 18, dehydration esterification reaction is started with 9/10 mole of adipic acid and 6/10 mole of diethylene glycol using an esterification catalyst. 1/10 mole of diethylene glycol monobutylether is added dropwise. At the last stage of distillation of water, is added 0.1 mole of octanol. Finally, small excess of octanol is added. In this manner, esterification is carried out. A product is obtained as a residual liquid from distillation. The results are shown in Table 2.

EXAMPLES 22, 23

Butoxyethyleneoxyethyl benzyl tetra(1,3-butanediyl adipate) (A-3)

[BEE(AX$_{13B}$)$_4$ABz]ethyldiethyleneoxyethyl benzyl tetra(1,3-butanediyl adipate) [EDEE(AX$_{13B}$)$_4$ABz]

TABLE 1

| | (A-1[REE(AX)$_m$AEER]) | | | | | | |
|---|---|---|---|---|---|---|---|
| | | Plasticizing | Volatile | Electric | softening | migration % | |
| Example | Viscosity | efficiency | loss | resistance | point | to PVC | to PE |
| 1 [BEEAX$_{13B}$AEEB] | 138 | 46 | 4.0 | 4.5 × 10$^9$ | −32.3 | 5.8 | 1.8 |
| 6 [BEEAX$_{12P}$AEEB] | 102 | 41 | 4.9 | 1.5 × 10$^9$ | −27.3 | 6.4 | 1.6 |
| 7 [BEEAX$_D$AEEB] | 260 | 54 | 4.4 | 2.3 × 10$^9$ | −27.1 | 5.2 | 1.2 |
| 8 [HEAX$_{13B}$AEH] | 170 | 54 | 2.4 | 1.3 × 10$^{10}$ | −5.2 | 4.2 | 0.7 |
| 9 [BEE(AX$_D$)$_2$AEEB] | 420 | 59 | 4.4 | 1.3 × 10$^9$ | −21.5 | 3.4 | 1.0 |
| 10 [BEE(AX$_{13B}$)$_3$AEEB] | 398 | 51 | 2.4 | 1.3 × 10$^{10}$ | −20.9 | 3.3 | 1.1 |
| 11 [BEE(AX$_{12P}$)$_3$EEB] | 301 | 53 | 3.1 | 1.1 × 10$^{10}$ | −20.3 | | |
| 12 [EEE(AX$_{13B}$)$_3$EEE] | 431 | 47 | 3.6 | 2.9 × 10$^9$ | −21.0 | 2.8 | 0.8 |
| 13 [HEE(AX$_{13B}$)$_3$EEH] | 493 | 49 | 3.3 | 4.4 × 10$^9$ | −21.0 | 2.6 | 1.1 |
| 14 [BzE(AX$_{13B}$)$_3$AEBz] | 613 | 54 | 3.4 | 3.2 × 10$^9$ | −11.3 | | |
| 15 [MeDEE(AX$_D$)$_3$AEDEMe] | 970 | 71 | 3.9 | 2.7 × 10$^9$ | −10.0 | 2.7 | 1.4 |
| 16 [BEE(AX$_{13B}$)$_8$AEEB] | 1569 | 56 | 2.4 | 2.0 × 10$^{10}$ | −11.5 | 1.5 | 1.0 |
| 17 [BEE(AX$_{13B}$)$_{13}$AEEB] | 1006 | 54 | 2.9 | 2.1 × 10$^{10}$ | −12.3 | 1.8 | 1.1 |
| | 1970 | 55 | 1.4 | 2.9 × 10$^{10}$ | −10.0 | 1.2 | 0.9 |

Hereinafter (A-2:[REE(AX)$_m$AEER]) will be explained.

A dehydration esterification reaction is started with 5/4 moles of adipic acid, and 4/4 mole of 1,3-butane diol using polyol polytitanic acid catalyst. At first, ¼ mole of the etheralcohol is added in portions and the reaction is caused to proceed while recycling water, and finally, ¼ mole of benzylalcohol is added to reduce the acid value, followed by addition of an amount for excess of the etheralcohol, 8.5 g or 4.5 g, to complete the esterification at an acid value of 2.5 or 3.0. After work-up, distillation results in the products having 871 cP and 968 cP as a residual liquid of distillation. Their plasticizing efficiencies are 54 and 53, respectively.

EXAMPLE 24

Butoxyethyleneoxyethyl benzyl tri(ethyleneoxyethanediyl adipate) [BEE(AX$_D$)$_3$ABz]

Using the same mole amounts of reaction as in Example 19, m=3, and using diethylene glycol as the diol, and benzylalcohol in place of octanol, a reaction is carried out and a product is obtained.

TABLE 2

| Example | Viscosity | (A-2[REE(AX)$_{m4}$EER]) Plasticizing efficiency | Volatile loss | Electric resistance | softening point | migration % to PVC | to PE |
|---|---|---|---|---|---|---|---|
| 18 [BEEAX$_{13B}$AO] | 137 | 47 | 3.9 | 8.8 × 10$^9$ | −26.5 | 4.3 | 1.9 |
| 19 [BEE(AX$_{13B}$)$_3$AO] | 338 | 49 | 2.8 | 5.9 × 10$^9$ | −18.9 | 2.6 | 1.2 cd |
| 20 [BEE(AX$_{13B}$)$_8$AO] | 883 | 53 | 2.1 | 1.3 × 10$^{10}$ | −13.3 | 2.1 | 0.8 |
| 21 [BEE(AX$_D$)$_2$AO] | 245 | 50 | 6.1 | 8.6 × 10$^9$ | −26.8 | | |
| 22 [BEE(AX$_{13B}$)$_4$ABz] | 871 | 54 | 2.3 | 7.6 × 10$^9$ | −12.6 | 2.1 | 0.6 |
| 23 [EDEE(AX$_{13B}$)$_4$ABz] | 968 | 53 | 2.2 | 6.8 × 10$^9$ | −11.4 | 2.3 | 0.7 |
| 24 [BEE(AX$_D$)$_3$ABz] | 837 | 59 | 3.2 | | −12.6 | 3.4 | 1.1 |

Hereinafter heterogeneous composite esters (A-3:[REEPX(AX)$_m$PEER] and [REEPX(AX)$_m$AR]) are explained.

EXAMPLE 25

Di-butoxyethyleneoxyethyl mono(1,3-butanediyl phthalate) [BEEPX$_{13B}$PEEB]

A mixture of 148 g of phthalic anhydride and 0.3 mole equivalent (27 g) of 1,3-butane diol is heated and stirred at 110° C. After 3 hours, 0.4 mole of diethylene glycol monobutylether is further added, and they are further heated for 3 hours to react the anhydride. Then, the equivalent amount (162 g) of the etheralcohol and 0.6 g of tetrabutoxytitanium as a catalyst are added, and added to an heat-activated solution to start dehydration esterification reaction, and when the acid value is 4.2, butanol is added. The esterification reaction is continued and is completed at an acid value of 0.2. After removal of the catalyst and work-up, distillation under reduced pressure is performed. A majority of dibutoxyethyleneoxy phthalate DBEEP is removed by distillation at 185°-230° C./0.5 mmHg and a product still containing some volatile materials boiling above 255° C./0.7 mmHg. Using the calculated amount of the high boiling alcohol as the terminal alcohol component and reducing the acid value by using low boiling butanol, the transesterification is minimized. As a result, phthalate composite esters having a relatively low viscosity is produced. Its viscosity is 249 cP, and its plasticizing efficiency is 52, and its softening point is −13.0° C.

EXAMPLE 26

Dibutoxyethyleneoxyethyl (1,3-butanediyl adipate phthalate) [BEEPX13BAX$_{13B}$PEEB]

To ⅔ mole of phthalic anhydride, is added ⅔ moles of diethylene glycol monobutylether. The anhydride is reacted at 110° C. for 3 hours by heating and stirring. ⅓ mole of adipic acid and ⅔ mole of 1,3-butane diol are added and 0.8 g of titanic acid solid catalyst is added to carry out dehydration esterification reaction. 25.4 ml of water is removed, and after removed of the catalyst, distillation is performed. Ten ml of forerun is removed and a product boiling 270° C./0.6 mmHg or higher, and having a viscosity of 1284 cP is obtained as a residual liquid.

EXAMPLE 27

Di-butoxyethyleneoxyethyl tetra(1,3-butanediyl adipate phthalate) [BEEPX$_{13B}$(AX$_{13B}$)$_3$PEEB]

By changing the molar ratio of the reaction of Example 26, ⅔ mole of phthalic anhydride and ⅔ mole of diethylene glycol monobutylether are reacted, and dehydration esterification reaction is carried out by adding 3/3 mole of adipic acid, 4/3 mole of 1,3-butane diol and a catalyst. After the reaction is complete, the catalyst is removed and distillation is performed. There is little forerun and the product is obtained as a residual liquid boiling above 270° C./0.5 mmHg or higher. The viscosity of the product is 1097 cP.

The composite ester in which both the terminal groups are ether-ester group has relatively low viscosity even if phthalic acid residual group is incorporated. However, by introduction of an aromatic group, the plasticizing efficiency becomes poorer. However, the migration property and electric properties are excellent. When composite esters and polyesters are formed, by-products low volatile materials are scarcely formed, which is a characteristic point.

EXAMPLE 28

Dibutoxyethyleneoxyethyl octa(1,3-butanediyl adipate phthalate) [BEEPX$_{13B}$(AX$_{13B}$)$_7$AEEB]

⅛ mole of phthalic anhydride and ⅛ mole of diethylene glycol monobutylether are reacted. Then, 8/8 mole of adipic acid, 8/8 mole of 1,3-butane diol, and ⅛ mole of the etheralcohol and a catalyst are added to carry out dehydration esterification reaction. A volatile material 7 ml is obtained from the distillation. The product is obtained as a residual liquid boiling above 280° C./0.4 mmHg. Its viscosity is 1671 cP.

EXAMPLES 29, 30

Butoxyethyl di-2-ethylhexyl tri- or octa-(1,3-butanediyl adipate phthalate) [BEEPX$_{13B}$(AX$_{13B}$)$_2$AO][BEEPX$_{13B}$(AX$_{13B}$)$_7$AO]

To a reaction product of 1/6 mole or 1/10 mole of phthalic anhydride and 1/6 mole or 1/10 mole of diethylene glycol monobutylether, is added 4/6 mole or 8/10 mole of adipic acid, 4/6 or 8/10 mole of 1,3-butane diol and 1/6 or 1/10 mole of 2-ethylhexanol and a catalyst to carry out dehydration esterification reaction. Foreruns 11 g and 6 g are removed in distillation, and the product boiling above 270° C./0.5 mmHg has a viscosity of 915 or 3060 cP.

EXAMPLE 31

Butoxyethyleneoxyethyl 2-ethylhexyl tetra(1,2-propanediyl adipate phthalate)[BEEPX12P(AX$_{12P}$)$_3$AO]

In the same manner as in Example 29, runs are carried out in which molar ratios of the reaction and diol are varied. To a reaction product of 1/5 mole of phthalic anhydride and 1/5 mole of diethylene glycol monobutylether, are added 4/5 mole of adipic acid, 4/5 mole of 1,2-propane diol and 1/5 mole of 2-ethylhexanol and a catalyst to carry out dehydration esterification reaction. After conventional treatment and distillation, 12 g of forerun and a product as residual liquid are obtained.

EXAMPLE 32

Methyldiethyleneoxyethyl 2-ethylhexyl tri(1,3-butanediyl adipate phthalate) [MeDEEPX13B(AX13B)$_2$AO]

In the same manner as in Example 29, the etheralcohol is changed. To a reaction liquid in which 1/6 mole of phthalic anhydride and 1/6 mole of triethylene glycol monomethylether are reacted, are added 4/6 mole of adipic acid, 4/6 mole of 1,3-butane diol and 1/6 mole of 2-ethylhexanol and a catalyst to carry out the reaction. A product is obtained as a residual liquid and has a viscosity of 926 cP.

used as a plasticizer, the volatility is about 2/3 compared with DOP.

EXAMPLE 34

Butoxyethyleneoxyethyl 2-ethylhexyl phthalate [BEEPO]

A reaction is carried out by adding ½ mole of phthalic anhydride and ½ mole of diethylene glycol monobutylether. A product is obtained by carrying out dehydration esterification reaction using ½ mole of 2-ethylhexanol and a small amount for the excess. As a result of distillation, DOP fraction boiling at 180°–195° C./0.5 mmHg is removed and a product is obtained as a residual liquid. The viscosity at 21° C. is 97 cP. A Japanese Patent Application has been filed by me for a process in which 1 mole of diethylene glycol monobutylether is used for transesterification. On that occasion, about half the amount of the products is the desired product and ¼ amount and ¼ amount are DOP and dibutoxyethyleneoxy phthalate, respectively. In this process, relatively pure objective product is obtained.

EXAMPLES 35 TO 37

Ethoxyethyleneoxyethyl 2-ethylhexyl phthalate [EEEPO], Methoxyethyleneoxyethyl 2-ethylhexyl phthalate [MeDEEPO], and Hexyloxyethyleneoxyethyl 2-ethylhexyl phthalate

TABLE 3

| Example | Visc. | P.E. | V.L. | E.R. | softening point | migration % to PVC | to PE |
|---|---|---|---|---|---|---|---|
| 25 [BEEPX$_{13B}$PEEB] | 249 | 52 | 1.8 | | −13.0 | | |
| 26 [BEEPX$_{13B}$AX$_{13B}$PEEB] | 1284 | 61 | 2.4 | 2.2 × 10$^{11}$ | −3.7 | 1.5 | 1.0 |
| 27 [BEEPX$_{13B}$(AX$_{13B}$)$_3$PEEB] | 1097 | 61 | 3.2 | 5.5 × 10$^{10}$ | −7.0 | 1.6 | 1.0 |
| 28 [BEEPX$_{13B}$(AX$_{13B}$)$_7$AEEB] | 1371 | 59 | 2.4 | 1.0 × 10$^{10}$ | −11.3 | 1.7 | 0.7 |
| 29 [BEEPX$_{13B}$(AX$_{13B}$)$_2$AO] | 915 | 54 | 2.8 | 2.3 × 10$^{10}$ | −8.7 | 2.3 | 1.1 |
| 30 [BEEPX$_{13B}$(AX$_{13B}$)$_7$AO] | 3060 | 56 | 2.8 | 2.3 × 10$^{10}$ | −7.6 | | 0.7 |
| 31 [BEEPX$_{12B}$(AX$_3$AO] | 1847 | 59 | 2.0 | 5.4 × 10$^{10}$ | −5.3 | 1.6 | |
| 32 [MeDEEPX$_{13B}$(AX$_{13B}$)$_2$AO] | 926 | 57 | 2.8 | 2.3 × 10$^{10}$ | −8.8 | | |

(Visc. = viscosity; P.E. = plasticizing efficiency; V.L. = volatile loss; E.L. = electric resistance)

Hereinafter (B:[REEPR']) will be explained.

EXAMPLE 33

Butoxyethyleneoxyethyl benzyl phthalate [BEEPBz]

One mole of phthalic anhydride and one mole of diethylene glycol monobutylether are heated and stirred at 100° to 110° C. After 3 hours, are added a calculated amount (one mole) of benzyl alcohol and a titanium catalyst to start dehydration esterification reaction. In a state when the acid value is decreased, a small excess amount of benzyl alcohol is supplemented to carry out dehydration esterification reaction. After the removal of the catalyst and washing with an alkali solution, distillation under reduced pressure is performed. After recovery of 43 g of forerun which is a low volatile fraction boiling at 200°–218° C./0.5 mmHg, 240 g of a product boiling at 219°–235° C./0.5 mmHg is obtained. The viscosity at 21° C. is 125 cP. When it is

[HEEPO]

In the same manner as in Example 34, equivalent amounts of phthalic anhydride and di- or tri-ethylene glycol monoalkylether are reacted and then, using a least possible excess amount of octanol, a diester wherein one terminal of phthalic acid is ether-ester, and the other terminal is alkyl can be produced. Their viscosities are 93, 89 and 124 cP, respectively. These compounds are of low volatility corresponding to their molecular weight and their volatile loss is about 60% of DOP. They are usable as a plasticizer. Their resistance to water is poorer when triethylene glycol is used than when diethylene glycol is used, and deteriorated as the alkyl group is lower alkyl group such as methyl. But the extent of deterioration of resistance to water is not significant and their plasticizing property and low temperature properties are somewhat improved.

TABLE 4

| Example | Viscosity | Plasticizing efficiency | Volatile loss | Electric resistance | softening point | migration % to PVC | to PE |
|---|---|---|---|---|---|---|---|
| 33 [BEEPBz] | 125 | 50 | 9.8 | 1.6 × 10$^{10}$ | −27.3 | 3.1 | 6.9 |
| 34 [BEEPO] | 97 | 48 | 9.2 | 9.0 × 10$^9$ | −23.2 | 3.5 | 3.7 |
| 35 [EEEPO] | 93 | 46 | 8.9 | 7.5 × 10$^9$ | −27.8 | 3.6 | 3.4 |
| 36 [MeDEEPO] | 89 | 46 | 8.6 | 6.6 × 10$^9$ | −17.8 | 3.9 | 2.4 |
| 37 [HEEPO] | 124 | 50 | 6.9 | 7.7 × 10$^{10}$ | −24.6 | 3.6 | 4.6 |

TABLE 4-continued

| Example | Viscosity | Plasticizing efficiency | Volatile loss | Electric resistance | softening point | migration % to PVC | to PE |
|---|---|---|---|---|---|---|---|
| Control DOP | 74 | 50 | 15.9 | $6.6 \times 10^{10}$ | −26.4 | 3.0 | 6.5 |

The following table summarizes the products and starting materials of the examples.

$R_1(OCH_2CH_2)_nO(COACOOXO)_mCOACO(OCH_2CH_2)_kOR_2$

| Ex | Product | m |
|---|---|---|
| 1 | [BEEAX$_{13B}$AEEB] | 1 |
| 2 | [BEEAX$_{13B}$AEEB] | 1 |
| 3 | [BEEAX$_{13B}$AEEB] | 1 |
| 4 | [BEEAX$_{13B}$AEEB] | 1 |
| 5 | [BEEAX$_{13B}$AEEB] | 1 |
| 6 | [BEEAX$_{12P}$AEEB] | 1 |
| 7 | [BEEAX$_D$AEEB] | 1 |
| 8 | [HEAX$_{13B}$AEH] | 1 |
| 9 | [BEE(AX$_D$)$_2$AEEB] | 2 |
| 10 | [BEE(AX$_{13B}$)$_3$AEEB] | 3 |
| 11 | [BEE(AX$_{12P}$)$_3$AEEB] | 3 |
| 12 | [EEE(AX$_{13B}$)$_3$AEEE] | 3 |
| 13 | [HEE(AX$_{13B}$)$_3$AEEH] | 3 |
| 14 | [BzE(AX$_{13B}$)$_3$AEBz] | 3 |
| 15 | [MeDEE(AX$_D$)$_3$AEDEMe] | 3 |
| 16 | [BEE(AX$_{13B}$)$_8$AEEB] | 8 |
| 17 | [BEE(AX$_{13B}$)$_{13}$AEEB] | 13 |
| 18 | [BEEAX$_{13B}$AO] | 1 |
| 19 | [BEE(AX$_{13B}$)$_3$AO] | 3 |
| 20 | [BEE(AX$_{13B}$)$_8$AO] | 8 |
| 21 | [BEE(AX$_D$)$_2$AO] | 2 |
| 22 | [BEE(AX$_{13B}$)$_4$ABz] | 4 |
| 23 | [EDEE(AX$_{13B}$)$_4$ABz] | 4 |
| 24 | [BEE(AX$_D$)$_3$ABz] | 3 |
| 25 | [BEEPX$_{13B}$PEEB] | 1 |
| 26 | [BEEPX$_{13B}$AX$_{13B}$PEEB] | 1 |
| 27 | [BEEPX$_{13B}$(AX$_{13B}$)$_3$PEEB] | 3 |
| 28 | [BEEPX$_{13B}$(AX$_{13B}$)$_7$AEEB | 7 |
| 29 | [BEEPX$_{13B}$(AX$_{13B}$)$_2$AO] | 2 |
| 30 | [BEEPX$_{13B}$(AX$_{13B}$)$_7$AO] | 7 |
| 31 | [BEEPX$_{12P}$(AX$_{12P}$)$_3$AO] | 3 |
| 32 | [MeDEEPX$_{13B}$(AX$_{13B}$)$_2$AO] | 2 |
| 33 | [BEEPBz] | 0 |
| 34 | [BEEPO] | 0 |
| 35 | [EEEPO] | 0 |
| 36 | [MeDEEPO] | 0 |
| 37 | [HEEPO] | 0 |

| | Starting material | | | | | |
|---|---|---|---|---|---|---|
| | HOOCACOOH | | HOXOH $R_1(OCH_2CH_2)_n$OH or $R_2(OCH_2CH_2)_k$OH | | | |
| Ex | A | X | $R_1$ | n | k | $R_2$ |
| 1 | (CH$_2$)$_4$ | CH$_2$CH$_2$(CH$_3$)CH | Bu | 2 | 2 | Bu |
| 2 | (CH$_2$)$_4$ | CH$_2$CH$_2$(CH$_3$)CH | Bu | 2 | 2 | Bu |
| 3 | (CH$_2$)$_4$ | CH$_2$CH$_2$(CH$_3$)CH | Bu | 2 | 2 | Bu |
| 4 | (CH$_2$)$_4$ | CH$_2$CH$_2$(CH$_3$)CH | Bu | 2 | 2 | Bu |
| 5 | (CH$_2$)$_4$ | CH$_2$CH$_2$(CH$_3$)CH | Bu | 2 | 2 | Bu |
| 6 | (CH$_2$)$_4$ | CH$_2$(CH$_3$)CH | Bu | 2 | 2 | Bu |
| 7 | (CH$_2$)$_4$ | CH$_2$CH$_2$OCH$_2$CH$_2$ | Bu | 2 | 2 | Bu |
| 8 | (CH$_2$)$_4$ | CH$_2$CH$_2$(CH$_3$)CH | Hx | 1 | 1 | Hx |
| 9 | (CH$_2$)$_4$ | CH$_2$CH$_2$OCH$_2$CH$_2$ | Bu | 2 | 2 | Bu |
| 10 | (CH$_2$)$_4$ | CH$_2$CH$_2$(CH$_3$)CH | Bu | 2 | 2 | Bu |
| 11 | (CH$_2$)$_4$ | CH$_2$(CH$_3$)CH | Bu | 2 | 2 | Bu |
| 12 | (CH$_2$)$_4$ | CH$_2$CH$_2$(CH$_3$)CH | Et | 2 | 2 | Et |
| 13 | (CH$_2$)$_4$ | CH$_2$CH$_2$(CH$_3$)CH | Hx | 2 | 2 | Hx |
| 14 | (CH$_2$)$_4$ | CH$_2$CH$_2$(CH$_3$)CH | Bz | 1 | 1 | Bz |
| 15 | (CH$_2$)$_4$ | CH$_2$CH$_2$OCH$_2$CH$_2$ | Me | 3 | 3 | Me |
| 16 | (CH$_2$)$_4$ | CH$_2$CH$_2$(CH$_3$)CH | Bu | 2 | 2 | Bu |
| 17 | (CH$_2$)$_4$ | CH$_2$CH$_2$(CH$_3$)CH | Bu | 2 | 2 | Bu |
| 18 | (CH$_2$)$_4$ | CH$_2$CH$_2$(CH$_3$)CH | Bu | 2 | 0 | 2EtHx |
| 19 | (CH$_2$)$_4$ | CH$_2$CH$_2$(CH$_3$)CH | Bu | 2 | 0 | 2EtHx |
| 20 | (CH$_2$)$_4$ | CH$_2$CH$_2$(CH$_3$)CH | Bu | 2 | 0 | 2EtHx |
| 21 | (CH$_2$)$_4$ | CH$_2$CH$_2$OCH$_2$CH$_2$ | Bu | 2 | 0 | 2EtHx |
| 22 | (CH$_2$)$_4$ | CH$_2$CH$_2$(CH$_3$)CH | Bu | 2 | 0 | Bz |
| 23 | (CH$_2$)$_4$ | CH$_2$CH$_2$(CH$_3$)CH | Et | 2 | 0 | Bz |
| 24 | (CH$_2$)$_4$ | CH$_2$CH$_2$OCH$_2$CH$_2$ | Bu | 2 | 0 | Bz |
| 25 | o-C$_6$H$_4$ | CH$_2$CH$_2$(CH$_3$)CH | Bu | 2 | 2 | Bu |
| 26 | o-C$_6$H$_4$/(CH$_2$)$_4$ | CH$_2$CH$_2$(CH$_3$)CH | Bu | 2 | 2 | Bu |
| 27 | o-C$_6$H$_4$/(CH$_2$)$_4$ | CH$_2$CH$_2$(CH$_3$)CH | Bu | 2 | 2 | Bu |
| 28 | o-C$_6$H$_4$/(CH$_2$)$_4$ | CH$_2$CH$_2$(CH$_3$)CH | Bu | 2 | 2 | Bu |
| 29 | o-C$_6$H$_4$/(CH$_2$)$_4$ | CH$_2$CH$_2$(CH$_3$)CH | Bu | 2 | 0 | 2EtHx |
| 30 | o-C$_6$H$_4$/(CH$_2$)$_4$ | CH$_2$CH$_2$(CH$_3$)CH | Bu | 2 | 0 | 2EtHx |
| 31 | o-C$_6$H$_4$/(CH$_2$)$_4$ | CH$_2$(CH$_3$)CH | Bu | 2 | 0 | 2EtHx |
| 32 | o-C$_6$H$_4$/(CH$_2$)$_4$ | CH$_2$CH$_2$(CH$_3$)CH | Me | 3 | 0 | 2EtHx |
| 33 | o-C$_6$H$_4$ | — | Bu | 2 | 0 | Bz |
| 34 | o-C$_6$H$_4$ | — | Bu | 2 | 0 | 2EtHx |
| 35 | o-C$_6$H$_4$ | — | Et | 2 | 0 | 2EtHx |
| 36 | o-C$_6$H$_4$ | — | Bu | 3 | 0 | 2EtHx |
| 37 | o-C$_6$H$_4$ | — | Hx | 2 | 0 | 2EtHx |

I claim:

1. A process for preparing simple esters, composite esters and polyesters with controlled molecular weight distribution having the formula $R_1(OCH_2CH_2)_nO(COACOOXO)_mCOACO(OCH_2CH_2)_kOR_2$ wherein n is 1 to 3; m is 0 to 13; k is 0 to 3 provided that k=0 when m=0; $R_1$ and $R_2$ are selected from the group consisting of an alkyl group of 1 to 10 carbon atoms and a benzyl group; A is an alkylene group of 2 to 4 carbon atoms or a residual group of an aromatic dicarboxylic acid; X is a straight or branched chain alkylene group, a residual group of a glycol selected from the group consisting of diethylene glycol, triethylene glycol, dipropylene glycol and tripropylene glycol, or a residual group of thiodiethanol; which process comprises the steps of (1) providing a starting material selected from the group consisting of
 (a) when m is not 0, a mixture of at least one dicarboxylic acid of the formula HOCOACOOH, wherein A is as defined above, and at least one diol of the formula HOXOH wherein X is as defined above, and
 (b) when m is 0, at least one dicarboxylic acid of the formula HOCOACOOH, wherein A is as defined above, (2) adding to said starting material an equivalent amount of at least one member selected from the group consisting of the monoalkylethers and benzylethers of ethylene glycol, diethylene glycol and triethylene glycol, or an equivalent amount of said at least one member and a monohydric alcohol having the formula $R_3$OH wherein $R_3$ is an alkyl group of 1 to 8 carbon atoms or benzyl, and (3) carrying out a dehydration esterification reaction during and after steps (1) and (2) in the presence of an alkoxy titanium catalyst or a solid polytitanic acid catalyst prepared from alkoxy titanium, said dehydration esterification reaction being carried out by first adding just enough of the monohydric alcohol or alcohols added in step (2) to esterify the acids and then finally adding a slight excess of the monohydric alcohol or alcohols added in step (2), said excess amount being enough to reduce any remaining acid value.

2. The process of claim 1 wherein m is 1 is greater.

3. The process of claim 1 wherein m is 0, k is 0, and the product has the formula $R_1(OCH_2CH_2)_nOCOACOOR_2$ wherein $R_1$, n, A and $R_2$ are as defined in claim 1.

4. The process of claim 1 wherein the dicarboxylic acid is phthalic, adipic or succinic acid.

5. The process of claim 1 wherein said member in step (2) is monoalkylether of ethylene glycol or diethylene glycol or triethylene glycol.

6. The process of claim 1 wherein an etheralcohol of the formula $R_1(OCH_2CH_2)_nOH$ is used wherein $R_1$ is butyl, hexyl, octyl or benzyl group.

7. The process of claim 1 wherein the diol in step (1)(a) is 1,2-, 1,3- or 1,4- butane diol, ethylene glycol, 1,2- or 1,3-propane diol or alkyl substituted diols of these diols, or ether alcohols selected from the group consisting of diethylene glycol, triethylene glycol, dipropylene glycol, and tripropylene glycol, thiodiethanol, and mixtures of at least two of these diols.

8. The process of claim 1 wherein the dicarboxylic acid used in step (1)(a) is phthalic acid and the final product is a heterogeneous composite ester containing phthalate ester.

9. A plasticizer comprising the product prepared by the process of claim 1.

10. A process for preparing a mixture of composite esters having the formula $R_1(OCH_2CH_2)_nO(COACOOXO)_{m'}COACO(OCH_2CH_2)_kOR_2$ and esters having the formula $R_1(OCH_2CH_2)_nOCOACO(OCH_2CH_2)_{k'}OR_2$ wherein n is 1 to 3; m' is 1 to 13; k is 0 to 3; k' is 1 to 3; $R_1$ is selected from the group consisting of an alkyl group of 1 to 10 carbon atoms and a benzyl group; A is an alkylene group of 2 to 4 carbon atoms or a residual group of an aromatic dicarboxylic acid; X is a straight or branched chain alkylene group, a residual group of a glycol selected from the group consisting of diethylene glycol, triethylene glycol, dipropylene glycol and tripropylene glycol, or a residual group of thiodiethanol; which process comprises the steps of (1) providing a starting material selected from the group consisting of
  (a) when m is not 0, a mixture of at least one dicarboxylic acid of the formula HOCOACOOH, wherein A is as defined above, and at least one diol of the formula HOXOH, wherein X is as defined above, and
  (b) when m is 0, at least one dicarboxylic acid of the formula HOCOACOOH, wherein A is as defined above, (2) adding to said starting material an equivalent amount of at least one member selected from the group consisting of the monoalkylethers and benzylethers of ethylene glycol, diethylene glycol and triethylene glycol, or an equivalent amount of said at least one member and a monohydric alcohol having the formula $R_3OH$ wherein $R_3$ is an alkyl group of 1 to 8 carbon atoms or benzyl, and (3) carrying out a dehydration esterification reaction during and after steps (1) and (2) in the presence of an alkoxy titanium catalyst or a solid polytitanic acid catalyst prepared from alkoxy titanium, said dehydration esterification reaction being carried out by first adding just enough of the monohydric alcohol or alcohols added in step (2) to esterify the acids and then finally adding a slight excess of the monohydric alcohol or alcohols added in step (2), said excess amount being enough to reduce any remaining acid value.

11. The process of claim 10 wherein the dicarboxylic acid is phthalic, adipic or succinic acid.

12. The process of claim 10 wherein said member in step (2) is monoalkylether of ethylene glycol or diethylene glycol or triethylene glycol.

13. The process of claim 10 wherein an etheralcohol of the formula $R_1(OCH_2CH_2)_nOH$ is used wherein $R_1$ is butyl, hexyl, octyl or benzyl group.

14. The process of claim 10 wherein the diol in step (1)(a) is 1,2-, 1,3- or 1,4- butane diol, ethylene glycol, 1,2- or 1,3-propane diol or alkyl substituted diols of these diols, or ether alcohols selected from diethylene glycol, triethylene glycol, dipropylene glycol, and tripropylene glycol, or thiodiethanol, or mixtures of two or more of these diols.

15. The process of claim 10 wherein the dicarboxylic acid used in step (1)(a) is phthalic acid and the final product is a heterogeneous composite ester containing phthalate ester.

16. A plasticizer comprising the product prepared by the process of claim 10.

* * * * *